(12) United States Patent
Marsh

(10) Patent No.: US 8,884,024 B1
(45) Date of Patent: Nov. 11, 2014

(54) PROCESS FOR PREPARING BENZISOTHIAZOLINONES

(71) Applicant: Titan Chemicals Limited, Tortola (VG)

(72) Inventor: Ian Roger Marsh, Kent (GB)

(73) Assignee: Titan Chemicals Limited, Road Town, Tortola (VG)

( * ) Notice: Subject to any disclaimer, the term of this patent is extended or adjusted under 35 U.S.C. 154(b) by 0 days.

(21) Appl. No.: 14/036,260

(22) Filed: Sep. 25, 2013

(51) Int. Cl.
*C07D 275/04* (2006.01)
*C07D 277/64* (2006.01)

(52) U.S. Cl.
CPC ............ *C07D 275/04* (2013.01); *C07D 277/64* (2013.01)
USPC ........................................................ 548/209

(58) Field of Classification Search
CPC .................................................... C07D 277/64
USPC ........................................................... 548/209
See application file for complete search history.

(56) References Cited

U.S. PATENT DOCUMENTS 4,871,754 A    10/1989  Bauer et al.

FOREIGN PATENT DOCUMENTS

CN          102807532        12/2012

OTHER PUBLICATIONS

Siegemund et al., "1,2-Benzisothiazol-3(2H) . . . and Biological Activity", Sulfur Reports, 2002, vol. 23, No. 3, pp. 279-319.

*Primary Examiner* — Samantha Shterengarts
*Assistant Examiner* — Amanda L Aguirre
(74) *Attorney, Agent, or Firm* — Clark & Brody

(57) ABSTRACT

N-alkylated 1,2-benzisothiazolin-3-ones can be prepared in good yield and good selectivity by reaction of the lithium salt of 1,2-benzisothiazolin-3-one with an electrophilic alkylating agent.

11 Claims, No Drawings

PROCESS FOR PREPARING BENZISOTHIAZOLINONES

This invention relates to processes for preparing benzisothiazolines. More especially the invention relates to processes for making N-substituted-1,2-benzisothiazolin-3-ones. Such materials, for example 2-methyl-1,2-benzoisothiazolin-3-one (CAS #2527-66-4) sometimes known as MeBIT and 2-butyl-1,2-benzoisothiazolin-3-one (CAS #4299-07-4) sometimes known as BuBIT have biocidal or fungicidal properties.

These materials have the structure shown in Formula 1

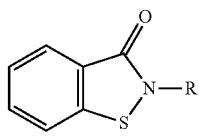

Formula 1 where R is straight chain or branched alkyl or benzyl.

Sulfur Reports, 2002, Vol 23, No. 3, pp 279-319 describes several synthetic routes to such materials.

CN102807532 describes the production of BuBIT (where R is n-Bu in Formula 1) by forming the sodium or potassium salt of BIT (where R is H in Formula 1) and then reacting the salt with bromobutane. A problem with this method is that N-alkylation does not proceed with good selectivity.

U.S. Pat. No. 4,871,754 describes the use of the lithium salt of 1,2-benzisothiazolin-3-one as a biocide.

It has now surprisingly been found that N-substituted 1,2-benzothiazoline-3-ones can be prepared with high selectivity by reacting the lithium salt of BIT with an alkylating or benzylating agent.

According to the invention there is provided a method of making an N-substituted 1,2-benzisothiazolin-3-one comprising reacting the lithium salt of 1,2-benzisothiazolin-3-one with a compound of formula R—X where R is $C_1$-$C_8$ straight chain or branched alkyl or benzyl and X is a good leaving group. In embodiments X is selected from the group consisting of Cl, Br, I, $SO_3Me$, triflate, mesyl, tosyl, besyl and sulfonate which may be substituted by one or more F atoms. Preferably R is Me or n-Bu. R—X can be selected from the group consisting of MeI, $Me_2SO_4$ and n-BuBr. Preferably the process is performed in the presence of a solvent selected from the group consisting of dimethylformamide, tetrahydrofuran, butanone, acetonitrile and acetone. The lithium salt of 1,2-benzisothiazolin-3-one is prepared by slurrying lithium hydroxide, 1,2-benzisothiazolin-3-one and a polar liquid such as ethanol, methanol, acetone, butanone, isopropanol, water and mixtures thereof, preferably industrial methylated spirits.

The lithium salt of BIT is known for example from U.S. Pat. No. 4,871,754. It can however be prepared slurrying BIT with a slight molar excess (for example 1 to 1.05 moles per mole) of lithium hydroxide. Either the monohydrate or anhydrous lithium hydroxide can be used. Generally the monohydrate is preferred on economic grounds. Slurrying can be performed in ethanol, either pure ethanol or ethanol containing water for example industrial methylated spirit "IMS" can be used. IMS is generally preferred on cost grounds. It is not essential to use ethanol and other materials such as methanol, acetone, butanone and isopropanol can be used either alone, especially where monohydrate is used, or in the presence of water. Mixtures of these materials may also be used. Typically slurrying is performed for 1 to 2 hours at elevated temperature for example reflux. After this time the slurry is allowed to cool, filtered and dried.

The lithium salt of BIT, however prepared, is then reacted with the appropriate alkylating or benzylating agent. The appropriate alkylating or benzylating agent will be chosen according to the N-substituted 1,2-benzothiazolin-3-one which it is desired to produce. Methyl and n-butyl are especially preferred but other alkyl such as $C_1$-$C_8$ straight or branched chain alkyl for example ethyl, propyl, isobutyl, and pentyl and 2-ethylhexyl can also be prepared. Benzyl which is optionally substituted by one or more alkyl such as $C_1$-$C_8$ straight or branched chain alkyl for example methyl, ethyl, propyl, butyl, isobutyl and pentyl can also be prepared.

Any of a wide range of electrophilic alkylating agents can be used. For example for the methyl substituted material, dimethyl sulfate or methyl iodide can be used. While it is possible to use stronger methylating agents such as methyl triflate or methyl fluorosulfonate it is not generally preferred in view of these materials greater expense and toxicity. For the butyl substituted material n-butyl bromide is preferably used.

The skilled worker in the art will have no difficulty in devising suitable alkylating or benzylating agent. Typically they will be alkyl or benzyl sulfates, halides especially bromides or iodides and sulfonates which may optionally be fluorinated with 1, 2 or 3 fluorine atoms, mesylates, besylates and tosylates.

Typically the alkylating agent is used in stoichiometric amount or slight molar excess for example 1 to 1.1 moles per mole of lithium salt.

Reaction is preferably performed in a polar aprotic solvent but this is not essential. Examples of suitable polar aprotic solvents include, dimethylformamide, acetonitrile, tetrahydrofuran, butanone, acetone and mixtures thereof. Typically the reaction is performed at ambient to elevated temperature for example reflux. The precise time taken for the reaction depends on a wide range of factors including temperature and the nature of the alkylating agent. Those skilled in the art will have no difficulty in devising suitable reaction conditions for example by experience or by monitoring the reaction by well known analytical techniques such as spectroscopy and chromatography. Once reaction is sufficiently far advanced the product can be isolated for example by filtering, evaporation of any solvent and distillation. If preferred the material can be converted to a salt for example hydrochloride by treatment with the appropriate acid such as hydrochloric acid.

Embodiments of the invention will now be described by reference to the following examples, production examples and comparative examples.

In each case purity and selectivity were determined by HPLC by reference to authentic samples. HPLC allowed the relative UV response factors for each material to be determined.

PRODUCTION EXAMPLE 1

Preparation of 1,2-benzisothiazolin-3-one lithium salt

Lithium hydroxide monohydrate (24.3 g, 0.58 mol) was added portionwise to a suspension of 1,2-benzisothiazolin-3-one paste (85% w/w, 100 g, 0.56 mol) in 350 ml industrial methylated spirit. The thick slurry was heated to 80° C. for 1.5 hours and allowed to cool. The resulting white solid was filtered off, washed with 2-butanone (50 ml), dried by suction and then oven dried at 70° C. The filtrate was warmed to concentrate to ~75% of its original volume and then cooled in an ice bath to effect further precipitation of the product, which was filtered off to give a second crop. The two crops were combined to give 62.6 g (71.2%) of 1,2-benzisothiazolin-3-one lithium salt in >99% purity.

PRODUCTION EXAMPLE 2

Preparation of 1,2-benzisothiazolin-3-one sodium salt

Sodium hydroxide solution (50% w/w, 57.0 g, 0.59 mol) was added dropwise to a stirred suspension of 1,2-benzisothiazolin-3-one paste (85% w/w, 100 g, 0.56 mol) in 300 ml industrial methylated spirit at 50° C. The resulting solution was concentrated to approximately 75% of its original volume until the solution showed slight turbidity. The mixture was allowed to cool, diluted with acetone (200 ml) and the solid filtered off. The solid was washed with 2×50 ml acetone, dried by suction and then oven dried at 80° C. The residual filtrate was concentrated and a second crop of crystals isolated, which were slurried in 100 ml acetone and isolated as above. The two crops were combined to give 91.2 g (92%) of 1,2-benzisothiazolin-3-one sodium salt in >99% purity.

EXAMPLE 1

Preparation of N-methyl-1,2-benzisothiazolin-3-one

To a stirred suspension of 1,2-benzisothiazolin-3-one lithium salt (10.0 g, 63.7 mmol) in butanone (30 ml) was added dropwise dimethyl sulfate (8.4 g, 6.4 ml, 66.9 mmol). The resulting slurry was stirred at room temperature for 90 hours. HPLC analysis showed greater than 96% alkylation of 1,2-benzisothiazolin-3-one lithium salt. The solvent was evaporated and the crude product distilled under reduced pressure to give a combined 77% yield of N-methyl-1,2-benzisothiazolin-3-one and 3-methoxy-2-benzisothiazole, with N-methyl-1,2-benzisothiazolin-3-one isolated in 94% purity. The ratio of N-alkylated material to O-alkylated material was 90:10.

EXAMPLE 2

Preparation of N-methyl-1,2-benzisothiazolin-3-one hydrochloride salt

To a stirred suspension of 1,2-benzisothiazolin-3-one lithium salt (10.0 g, 63.7 mmol) in acetone (30 ml) was added dropwise dimethyl sulfate (8.4 g, 6.4 ml, 66.9 mmol). The resulting slurry was stirred at room temperature for 24 hours. HPLC analysis showed greater than 99.5% alkylation of 1,2-benzisothiazolin-3-one lithium salt. The reaction mixture was diluted with methyl ethyl ketone (30 ml), filtered and the solid residues washed with 2-butanone (2×10 ml). The filtrate and washings were combined and concentrated hydrochloric acid (37% w/w, 10.0 ml) added dropwise.

The resulting N-methyl-1,2-benzisothiazolin-3-one hydrochloride salt was filtered off, washed with pentane (2×25 ml) and dried in vacuo. A second crop of N-methyl-1,2-benzisothiazolin-3-one hydrochloride salt was isolated from the filtrate to give a combined yield of 10.9 g (85%) in >99% purity. The ratio of N-alkylated material to O-alkylated material was 92.8:7.2.

EXAMPLE 3

Preparation of N-butyl-1,2-benzisothiazolin-3-one

A mixture of 1,2-benzisothiazolin-3-one lithium salt (1.0 g, 6.4 mmol) and 1-bromobutane (0.9 g, 6.7 mmol) in DMF (3.0 ml) was stirred at ambient temperature for 18 hours and 60° C. for 2 hours. HPLC analysis showed greater than 94% alkylation of 1,2-benzisothiazolin-3-one lithium salt. The mixture was allowed to cool and diluted with water (10 ml). The aqueous phase was decanted off and the resulting oil washed with water (2×5 ml) to yield the crude product as a mixture of N-butyl-1,2-benzisothiazolin-3-one and 3-butoxy-1,2-benzisothiazolin-3-one in 79:21 ratio.

EXAMPLE 4

Preparation of N-methyl-1,2-benzisothiazolin-3-one

To a stirred suspension of 1,2-benzisothiazolin-3-one lithium salt in THF (3 ml per gram of BIT salt) was added methyl iodide (1.1 molar equivalents). The resulting slurry was stirred at ambient temperature for 72 hours. HPLC analysis showed greater than 97% alkylation of 1,2-benzisothiazolin-3-one lithium salt. The mixture was allowed to cool and the crude product isolated as a mixture of N-methyl-1,2-benzisothiazolin-3-one and 3-methoxy-1,2-benzisothiazolin-3-one in 98.8:1.2 ratio.

COMPARATIVE EXAMPLE 1

Preparation of N-butyl-1,2-benzisothiazolin-3-one

A mixture of 1,2-benzisothiazolin-3-one paste (85% w/w, 20.0 g, 0.11 mol), potassium carbonate (30.0 g, 0.22 mol) and 1-bromobutane (16.9 g, 0.12 mol) in acetonitrile (200 ml) was stirred at 50° C. for 23 hours. HPLC analysis showed greater than 99% alkylation of 1,2-benzisothiazolin-3-one. The mixture was allowed to cool and diluted with water (400 ml). The aqueous phase was decanted off and the precipitated oil dried over magnesium sulfate and filtered to yield 22.4 g (96%) of the crude product as a mixture of N-butyl-1,2-benzisothiazolin-3-one and 3-butoxy-1,2-benzisothiazolin-3-one in 45:55 ratio. Distillation under reduced pressure enabled isolation of N-butyl-1,2-benzisothiazolin-3-one in 95% purity.

COMPARATIVE EXAMPLE 2

Preparation of N-butyl-1,2-benzisothiazolin-3-one

N-butyl-1,2-benzisothiazolin-3-one was prepared using the procedure reported in CN102807532.

A mixture of 1,2-benzisothiazolin-3-one sodium salt (1.0 g, 5.8 mmol) and 1-bromobutane (2.0 g, 14.4 mmol) in DMF (0.4 g) was stirred at 85° C. for 5 hours. HPLC analysis showed greater than 99% alkylation of 1,2-benzisothiazolin-3-one sodium salt. The mixture was allowed to cool and diluted with 10% aqueous hydrochloric acid (10 ml). The aqueous phase was decanted off and the resulting oil washed with water (2×5 ml) to yield 0.9 g (76%) of the crude product as a mixture of N-butyl-1,2-benzisothiazolin-3-one and 3-butoxy-1,2-benzisothiazolin-3-one in 56:44 ratio.

It will be seen from the results that the process of the invention proceeds with greater selectivity for the desired N-alkylated material than other processes

The invention claimed is:

1. A method of making an N-substituted 1,2-benzisothiazolin-3-one comprising reacting the lithium salt of 1,2-benzisothiazolin-3-one with a compound of formula R—X where R is $C_1$-$C_8$ straight chain or branched alkyl or benzyl and X is selected from the group consisting of Cl, Br, I, $SO_3Me$, triflate, mesyl, tosyl, besyl and sulfonate which may be substituted by one or more F atoms.

2. The method of claim 1 wherein R is Me or n-Bu.

3. The method of claim 1 wherein R is Me or n-Bu.

4. The method of claim 1 wherein R—X is selected from the group consisting of MeI, $Me_2SO_4$ and n-BuBr.

5. The method of claim 1 performed in the presence of a solvent selected from the group consisting of dimethylformamide, tetrahydrofuran, butanone, acetonitrile and acetone.

6. The method of claim 1 wherein said lithium salt of 1,2-benzisothiazolin-3-one is prepared by slurrying lithium hydroxide, 1,2-benzisothiazolin-3-one and a polar liquid.

7. The method of claim 5 wherein said lithium salt of 1,2-benzisothiazolin-3-one is prepared by slurrying lithium hydroxide, 1,2-benzisothiazolin-3-one and a polar liquid.

8. The method of claim 6 wherein said polar liquid is selected from the group consisting of ethanol, methanol, acetone, butanone, isopropanol, water and mixtures thereof.

9. The method of claim 8 wherein said polar liquid is industrial methylated spirits.

10. The method of claim 7 wherein said polar liquid is selected from the group consisting of ethanol, methanol, acetone, butanone, isopropanol, water and mixtures thereof.

11. The method of claim 10 wherein said polar liquid is industrial methylated spirits.

\* \* \* \* \*